US00PP30342P2

(12) United States Plant Patent
Hansoti

(10) Patent No.: US PP30,342 P2
(45) Date of Patent: Apr. 2, 2019

(54) ***SANSEVIERIA* PLANT NAMED 'HANSOTI20'**

(50) Latin Name: *Sansevieria trifasciata*
Varietal Denomination: Hansoti20

(71) Applicant: Ashish Hansoti, Mumbai (IN)

(72) Inventor: Ashish Hansoti, Mumbai (IN)

( * ) Notice: Subject to any disclaimer, the term of this patent is extended or adjusted under 35 U.S.C. 154(b) by 0 days.

(21) Appl. No.: 15/732,747

(22) Filed: Dec. 21, 2017

(51) Int. Cl.
*A01H 5/00* (2018.01)

(52) U.S. Cl.
USPC ..... Plt./382
CPC ..... *A01H 5/00* (2013.01)

(58) Field of Classification Search
USPC ..... Plt./382
CPC ..... A01H 5/00
See application file for complete search history.

*Primary Examiner* — Kent L Bell
(74) *Attorney, Agent, or Firm* — Cassandra Bright

(57) ABSTRACT

A new and distinct *Sansevieria* cultivar named 'HANSOTI20' is disclosed, characterized by bright variegated foliage with different green tones in the form of linear bands along the length of the leaf, contrasting with a base background color of yellowish cream and bright green colored margin bands in the leaf blade. Foliage has a narrow bright green marginal band. Plants require little water, having a moderate tolerance for drought, and are also tolerant of very wet conditions. The new variety is a *Sansevieria*, typically produced as an indoor ornamental plant.

6 Drawing Sheets

Figure 1:
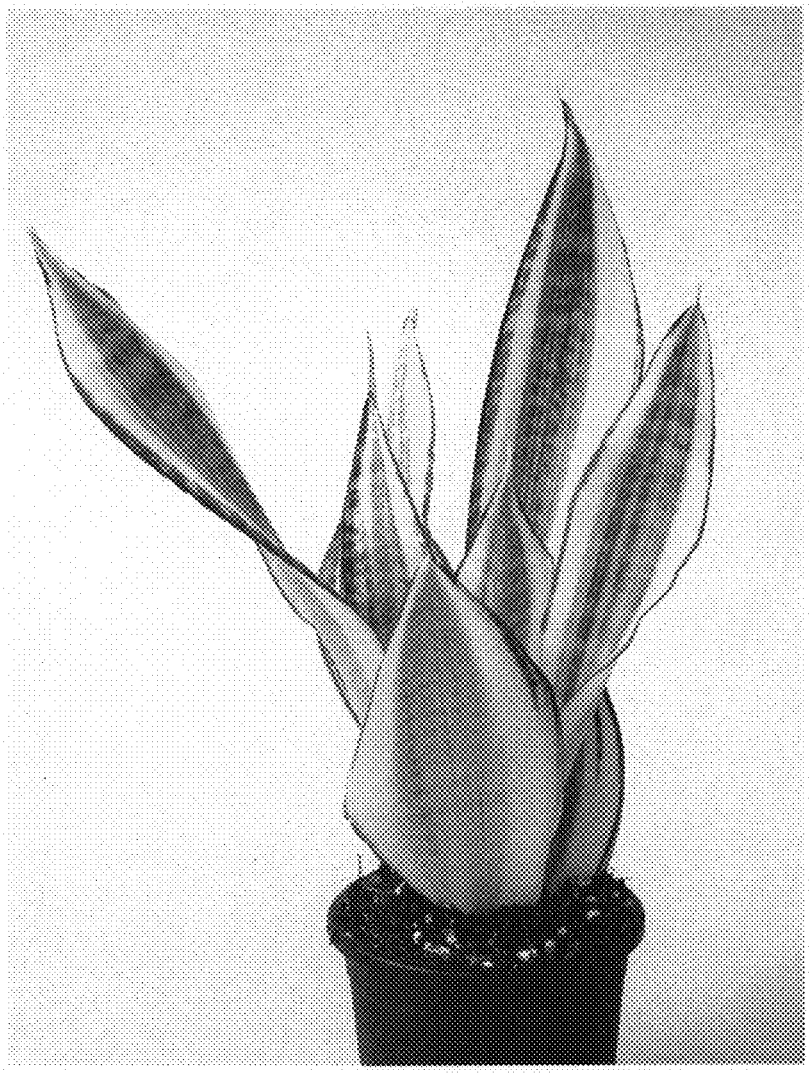

Latin name of the genus and species: *Sansevieria trifasciata.*

Variety denomination: 'HANSOTI20'.

BACKGROUND OF THE INVENTION

The present invention relates to a new and distinct cultivar of *Sansevieria* plant, botanically known as *Sansevieria trifasciata*, of the family Ruscaceae, hereinafter referred to by the cultivar name 'Hansoti20'.

*Sansevieria* is a monocotyledonous plant with fleshy, succulent leaves which are available in a huge range of species, varieties and cultivars as an outdoor ornamental plant (under tropical conditions) or as indoor plants.

The new *Sansevieria* 'Hansoti20' was discovered and selected by Mr. Ashish Hansoti, as a single aberrant plant within a planting of *Sansevieria* 'Futura Superba' (an unpatented widely grown cultivar) at Village Asle, District Satara, Maharashtra State in Western India. The new variety originated as a naturally-occurring whole plant mutation of the *Sansevieria* variety 'Futura Superba' (unpatented) in January 2014.

Asexual reproduction of the new *Sansevieria* cultivar by vegetative cuttings was first performed in November 2014 in Village Asle, District Satara, Maharashtra State in Western India and it was seen that the distinctive combination of characteristics of the new cultivar reproduced true to type as long as the propagation was done through side shoots (basal suckers) originating from the base of the originally discovered plant. Thus, it can be said that the new cultivar reproduces true to type through side shoots (basal suckers).

BRIEF SUMMARY OF THE INVENTION

The following traits have been repeatedly observed and are determined to be unique characteristics of 'Hansoti20', which in combination distinguish this *Sansevieria* as a new and distinct cultivar:

1. Bright variegated foliage with different green tones in the form of linear bands along the length of the leaf, contrasting with a base background color of yellowish cream and bright green colored margin bands in the leaf blade.
2. Bright green marginal band of 1 to 15 mm wide.
3. 25-25 cm plant height with average of 5 to 7 leaves per plant.
4. Needs less water and is moderately drought tolerant but still capable to growing in very wet conditions of the Indian Monsoon.

The new variety 'Hansoti20' is considered a variety of *Sansevieria* in the group denominated as "Compact *Sansevieria* plants". The new variety presents an average of 7 leaves per plant when it reaches its maturity (between 8-10 months).

The new variety has an erect growth habit and the entire plant can reach a height range between 25 and 35 cm. The leaves are of medium width (7 to 9 cm average measured at the widest part of the mature leaf under good growing conditions) and lanceolate with a firm, waxy texture. The blades are thick or fleshy and very slightly wavy. This variety also has an inverted triangle shape like most *Sansevierias* of the compact group.

The new variety is moderately drought tolerant and adapts well to conditions of bright light and heavy shade (exterior and interior).

The leaves show a bright variegated coloration, with vertical central wide band and occasional thin bands on a background of creamy yellow. This creamy color covers or overlay the central dark band to varying degrees so that this dark band can appear anywhere between a bright green to a lighter greyish green.

Overall color also depends on amount of light available—under higher shade overall color is darker and more yellowish; under higher light color is paler. The base creamy color varies from 7B to 8D (The former under more shade and latter under more light).

The central broad band shows green colorations varying from a dark green similar to 139A to a lighter color similar to 148D or 147C. However, due to extreme variability of shade and the overlying creamy coloration it is difficult to pin point the exact shade.

Each leaf has a marginal band that is brighter green and varies in width from just 1 to 15 mm. This marginal band, again variable in color, has little or no creamy overlay and so appears brighter. Color varies from near 144A to near 139A.

Superimposed on all the above are faint but visible lighter horizontal cross-banding (typical of broad leaved *Sansevierias* including *Sansevieria trifasciata* 'Futura Superba') that is more obvious over darker central and marginal bands and very faint and hardly noticeable across the creamy base color.

Backside of the leaves is similarly colored with wide central darker band and thinned marginal bands. However, usually the whole of the backside of the leaf is more uniform due to thicker overlying layer of cream so that the darker vertical bands are less distinct that on the front or top of the leaf.

Young shoots are obviously paler with a wide central band of color similar to 147C on inside of leaf and similar to 148C on the outside and a very pale background color of 2D. Marginal band is brighter green. In emerging pups the horizontal banding is more prominent especially on the margins.

PARENTAL COMPARISON

Plants of the new *Sansevieria* 'Hansoti20' differ from plants of the parental cultivar 'Futura Superba' (unpatented) in the characteristics described in Table 1.

TABLE 1

Comparison of New and Parental variety

| Characteristic | Parent 'Futura Superba' | New cv 'Hansoti20' |
|---|---|---|
| 1. Overall Color | Dark green with border | Golden color with green bands |
| 2. Border | Yellow border 3 to 15 mm | Bright green border 1 to 15 mm |
| 3. Leaf shape | Straight, reflexed with age | Straight, somewhat twisted |
| 4. Vigor | Slightly slower | Somewhat more vigorous |

The variety 'Futura Superba' gave rise to the variety 'Hansoti20'. The 'Futura Superba' variety is also considered part of the "compact *Sansevieria* group". 'Futura Superba' shows less vigor than 'Hansoti20', has fewer leaves per plant (4-5), with a narrower leaf with an average leaf width of 6.5 cm (measured in the middle of the mature leaf.) The growth habit is erect and presents wide leaves supported in a rosette. The entire plant can reach a size from 30-40 cm. The plant has, as for 'Hansoti20', an inverted triangle shape. The leaves are lanceolate with a waxy texture.

Overall the plants of 'Futura Superba' look greyish dark green with very distinct creamy to light green border about 3 to 15 mm wide and has no background creamy coloration while Hansoti 20 presents as a much brighter, lighter creamy yellow plant with wide green central band with greyish overlay and a brighter green, thinner marginal band. The cream background on the leaves and a thin layer of this creamy color on the green central band effectively gives the plant a more "Golden" appearance. This overall difference in appearance is striking.

In addition, leaves of the parent 'Futura Superba' are relatively straight and erect and with a slight twist along the length as they mature while 'Hansoti20' leaves are distinctly arched backwards and with little or no twisting along the length as they mature.

Newly emerging pups (side shoots) of 'Futura Superba' are also darker and with distinct creamy wide border along margins.

COMMERCIAL COMPARATORS

The new variety 'HANSOTI20' can be compared to the commercial variety known as *Sansevieria* 'Yellow Stripe', unpatented. 'HANSOTI20' is similar to 'Yellow Stripe' in most horticultural characteristics. The new variety however differs in the following:

1. 'HANSOTI20' has Yellow striping along leaf edges banded by a bright green margin. 'Yellow Stripe' has narrower Yellow-Green striping and no green margin.
2. Foliage of 'HANSOTI20' are more outwardly arching than foliage of 'Yellow Stripe'.
3. 'Yellow Stripe' has strong horizontal banding variegation, 'Hansoti20' has weak horizontal banding variegation.

The new variety 'HANSOTI20' can be compared to the commercial variety known as *Sansevieria* 'Ocean Star', unpatented. 'HANSOTI20' is similar to 'Ocean Star' in most horticultural characteristics. The new variety however differs in the following:

1. 'HANSOTI20' has Yellow striping along leaf edges banded by a bright green margin. 'Ocean Star' has narrower, lighter yellow striping and no green margin.
2. Plants of 'Ocean Star' shorter, forming a low growing rosette. Plants of 'HANSOTI20' are at least twice as tall and upright with a slight outward arch.
3. Foliage of 'Hansoti20' is narrower than foliage of 'Ocean Star'.

The new variety 'HANSOTI20' can be compared to the commercial variety known as *Sansevieria* 'Black Gold', unpatented. 'HANSOTI20' is similar to 'Black Gold' in most horticultural characteristics. The new variety however differs in the following:

1. 'HANSOTI20' has Yellow striping along leaf edges banded by a bright green margin. 'Blac, Gold' has narrower, lighter yellow striping and no green margin.
2. Foliage of 'HANSOTI20' are more outwardly arching than foliage of 'Black Gold'.
3. Foliage of 'Hansoti20' is broader than foliage of 'Black Gold'.

BRIEF DESCRIPTION OF THE PHOTOGRAPHS

The accompanying photographs illustrate the overall appearance of the new *Sansevieria* cultivar 'Hansoti20' showing the colors as true as is reasonably possible with colored reproductions of this type. Colors in the photographs may differ slightly from the color value cited in the detailed botanical description which accurately describe the color of 'Hansoti20'.

FIG. 1: Shows a side view of an eight-month old plant of *Sansevieria* 'Hansoti20' in a 15 cm diameter pot.

Figure 2:
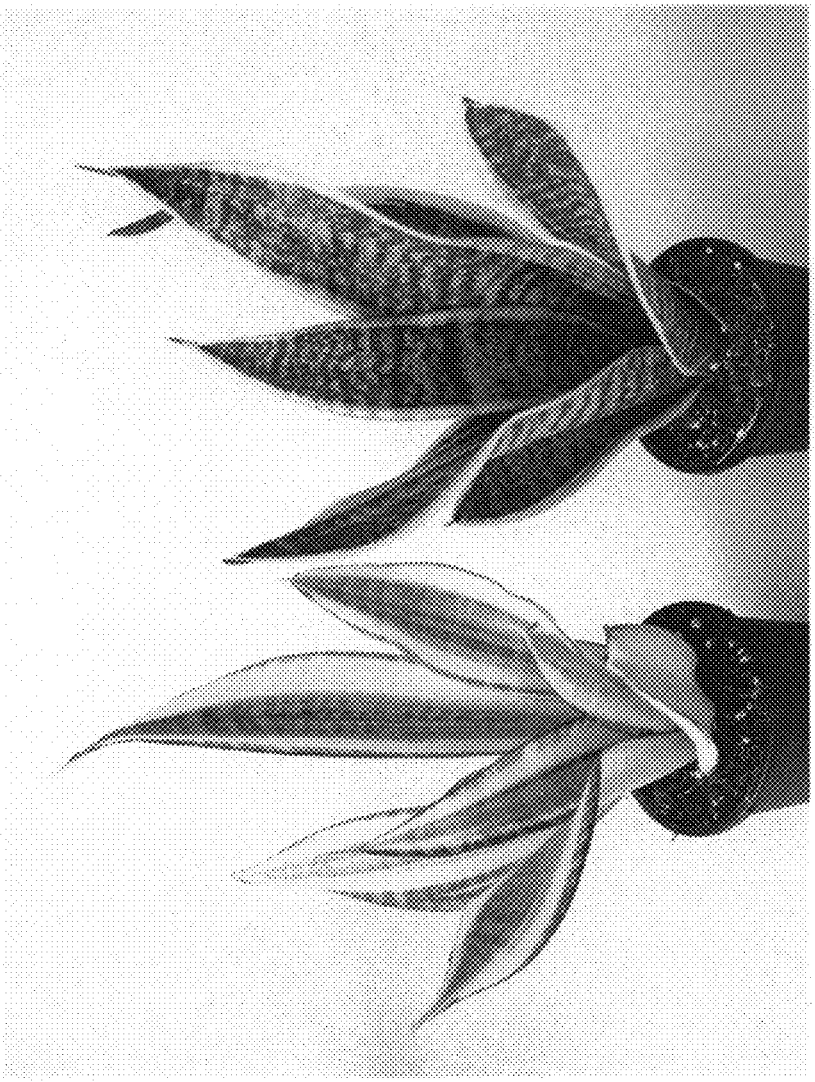

FIG. 2: Shows a side view comparing a plant of 'Hansoti20' with a comparable size plant of 'Futura Superba'

Figure 3:
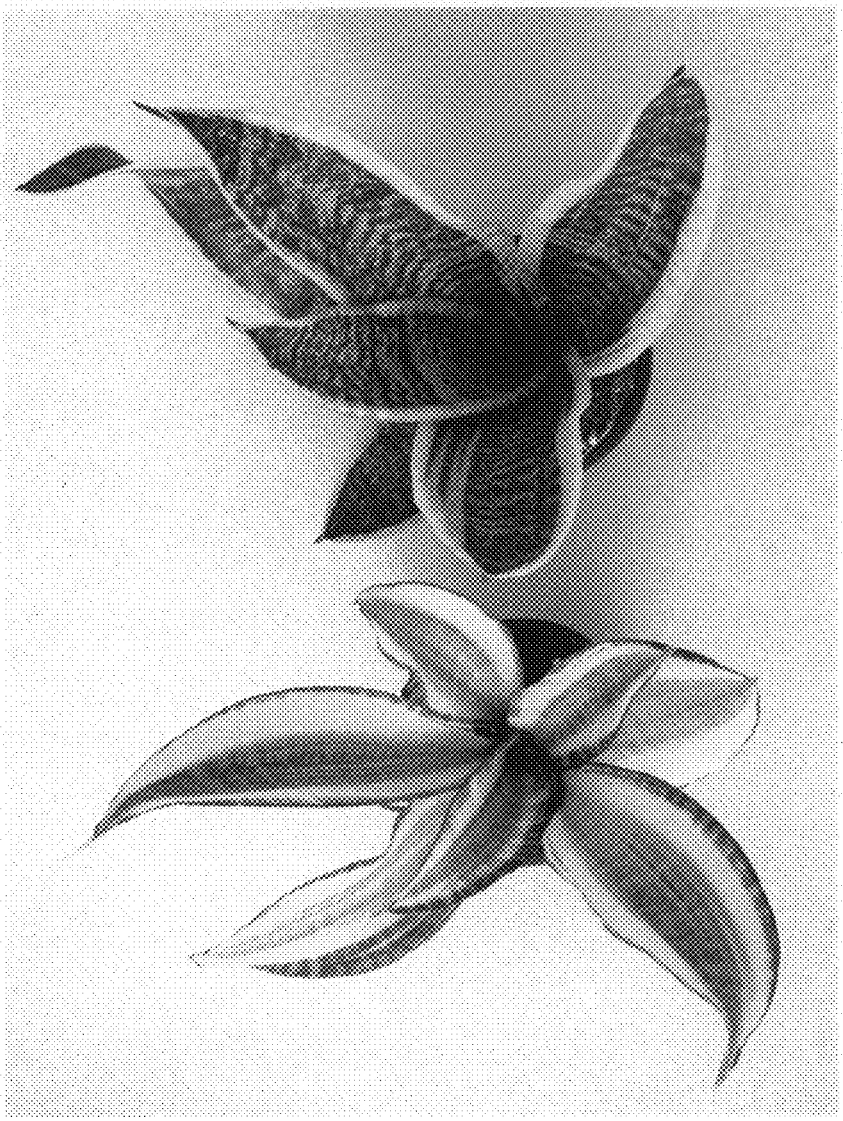

FIG. 3: Shows a top view comparing a plant of 'Hansoti20' with a comparable size plant of 'Futura Superba'

Figure 4:
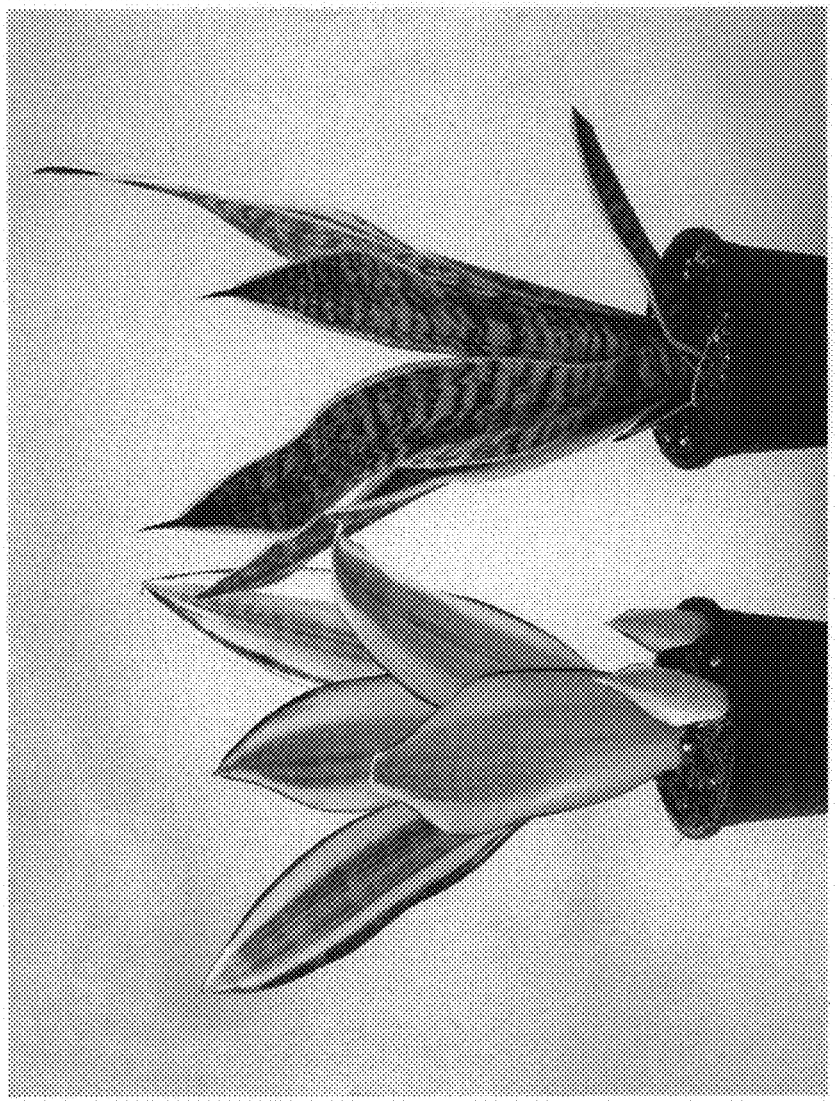

FIG. 4: Shows side views of 'Hansoti20' along with 'Superba compact' placed so as to show the back sides of leaves. Also seen are the much paler pups of 'Hansoti20'.

Figure 5:
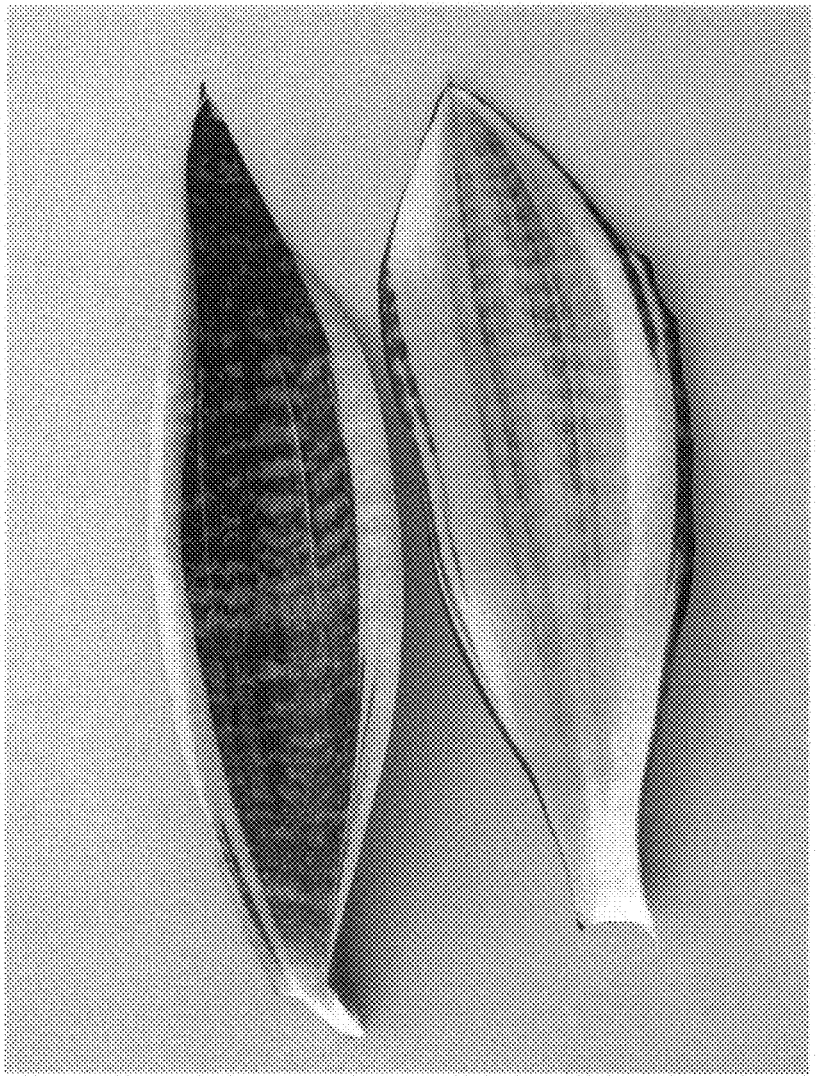

FIG. 5: Shows a close-up view of the upper side of a typical mature leaf of 'Hansoti20' side by side with a similarly mature leaf of 'Futura Superba'

Figure 6:
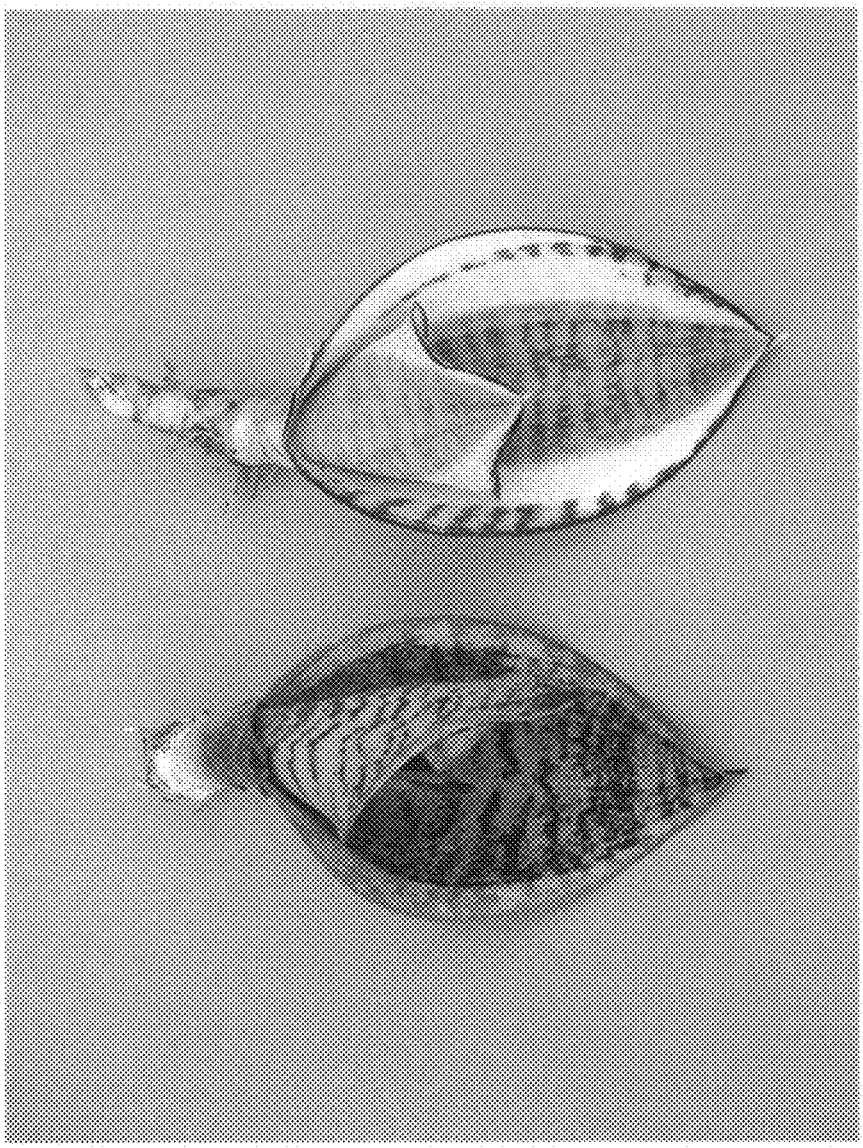

FIG. 6: Shows a close up of immature pups of 'Hansoti20' besides a similarly aged pup of 'Futura Superba'

DETAILED BOTANICAL DESCRIPTION

The new *Sansevieria* 'Hansoti20' has not been observed under all possible environmental conditions. The phenotype of the new cultivar may vary with variations in environment such as temperature, light intensity, fertilizer levels and composition and day length without any change in the genotype of the plant.

The aforementioned photographs, together with the following observations, measurements and values describe the new *Sansevieria* cultivar 'Hansoti20' as grown in an open Polyhouse (High Tunnel) at Village Asle, District Satara, Maharashtra State in Western India, conditions which closely approximate those generally used in commercial practice. Average temperature in Asle is 26° C. during the day and 20° C. at night. Plants grow under natural light conditions.

This crop gets nearly constant fertilization to increase production—a CLF—Constant Liquid Feed at approximately 150 ppm N, 30 ppm P and 150 ppm K is used along with micronutrients. Production is closely related with proper and complete plant nutrition and an open soilless growing media based on coconut coir. At this stage plants are grown in plastic pots with a view to grow in the ground once stocks are sufficiently built up.

Color references are made to The Royal Horticultural Society Color Chart (R.H.S.), (April 2009) except where general colors of ordinary significance are used.

The photographs and descriptions were taken during the rainy season in Asle, District Satara, Maharashtra State, India when outdoor day temperature was 23° C. to 25° C. The age of the plants described is 6-8 months.

Botanical classification: *Sansevieria trifasciata* 'HANSOTI20'.

General information:

- *Parentage.*—*Sansevieria trifasciata* 'Futura Superba' (unpatented).
- *Optimal growth conditions.*—
- *Light intensities.*—High adaptability to outdoor or indoor conditions.
- *Temperature.*—Day: 20° C. to 38° C. Night: 12° C. to 25° C.
- *Temperature tolerance.*—Tolerant to a low temperature of about 10° C. and a high temperature of 38° C. and above — very heat tolerant.
- *Fertilization.*—Constant feed of 150 ppm N, 30 ppm P and 150 ppm K is used along with micronutrients with occasional leaching.
- *Growth regulators.*—Not necessary.

Propagation:

- *Typical.*—Side suckers which come true to type.
- *Rooting habit and description.*—Rhizomes, with short roots. Cream to brown, not accurately measured with R.H.S. chart.
- *Time to initiate roots.*—15 to 20 days at 20 to 25° C.
- *Time to produce a rooted potted plant.*—About 90 days at 25° C. to 30° C.

Plant:

- *General appearance and form.*—
- *Height.*—About 30 cm when grown in pots.
- *Spread.*—About 25 to 35 cm when grown when grown in 15 cm size container.
- *Form.*—Monocot; leaf bases arranged in a rosette around growth point.
- *Shape.*—Inverted triangle.
- *Growth rate and habit.*—About 2 cm per week; upright.

Foliage:

- *Quantity.*—About 5 to 7.
- *Arrangement and attachment.*—Single, alternate; leaf bases arranged in a rosette around central growth point.
- *Leaf length.*—About 30 cm.
- *Leaf width.*—About 9 cm.
- *Overall shape of leaf.*—Lanceolate.
- *Apex shape.*—Acute, triangular.
- *Base shape.*—Truncate.
- *Margin.*—Entire. Sharp, smooth.
- *Texture.*—Upper Surface: smooth and waxy texture.
- *Texture.*—Under Surface: smooth and waxy texture.
- *Pubescence.*—None.
- *Color of mature leaf.*—Upper Surface: Basal cream color near 7B to 8D with dark central band varying from 139A to 148D or 147C — exact shade difficult to pinpoint because cream color overlays the central green band.
- *Margins.*—Bright yellow-green RHS 144A and/or green 139A.
- *Crossbanding.*—As typical for many *Sansevieria* but somewhat less prominent.
- *Venation.*—Pattern: Longitudinal/parallel leaf shape.
- *Venation color.*—Indistinguishable from leaf blade.
- *Leaf fragrance.*—None.

Other:

- *Inflorescence description.*—Flowers not observed to date.
- *Weather resistance.*—Moderately drought tolerant.
- *Pest resistance.*—Reasonably resistant to pests, susceptible to root mealybugs.
- *Disease resistance.*—Occasionally shows Anthracnose and leaf spots but largely disease free from clean mother stock.
- *Fruit/seed production.*—No fruits/seeds detected to date.

What is claimed is:

1. A new and distinct cultivar of *Sansevieria* plant named 'HANSOTI20' as herein illustrated and described.

* * * * *